US012606504B2

(12) United States Patent
Huang et al.

(10) Patent No.: US 12,606,504 B2

(45) Date of Patent: Apr. 21, 2026

(54) METHODS FOR MAKING ETHYLENE AND METHODS FOR MAKING PROPYLENE

(71) Applicant: Saudi Arabian Oil Company, Dhahran (SA)

(72) Inventors: Haitao Huang, Al Khobar (SA); Mohammad A. Alabdullah, Al Khobar (SA); Mosab T. Kheyami, Dhahran (SA); Yufeng He, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 119 days.

(21) Appl. No.: 18/461,891

(22) Filed: Sep. 6, 2023

(65) Prior Publication Data

US 2025/0074846 A1 Mar. 6, 2025

(51) Int. Cl.

| | |
|---|---|
| ***C07C 6/04*** | (2006.01) |
| ***C07C 4/06*** | (2006.01) |
| ***C07C 5/25*** | (2006.01) |

(52) U.S. Cl.

CPC .................. *C07C 6/04* (2013.01); *C07C 4/06* (2013.01); *C07C 5/25* (2013.01); *C07C 2529/06* (2013.01)

(58) Field of Classification Search

CPC ............ C07C 611/06; C07C 6/04; C07C 4/06

See application file for complete search history.

(56) References Cited

U.S. PATENT DOCUMENTS

| | | | | |
|---|---|---|---|---|
| 8,153,851 | B2 * | 4/2012 | Gartside | C07C 11/06 585/324 |
| 10,059,645 | B2 | 8/2018 | Shaikh et al. | |
| 10,214,466 | B2 | 2/2019 | Shaikh et al. | |
| 2010/0041930 | A1 | 2/2010 | Gartside et al. | |

* cited by examiner

*Primary Examiner* — Sharon Pregler

(74) *Attorney, Agent, or Firm* — DINSMORE & SHOHL LLP

(57) ABSTRACT

Described herein are methods for converting butene. In some embodiments, butene is converted to an ethylene-containing products. In additional embodiments, butene is converted to an propylene-containing products. In additional embodiments, butene is selectively converted to an ethylene-containing product and a propylene-containing product. These methods generally include metathesis and cracking reactions, as described.

20 Claims, 4 Drawing Sheets

METHODS FOR MAKING ETHYLENE AND METHODS FOR MAKING PROPYLENE

TECHNICAL FIELD

Embodiments of the present disclosure generally relate to chemical processing and, more specifically, to processes and systems utilized to make ethylene and/or propylene.

BACKGROUND

Ethylene and propylene are basic intermediates used by a large portion of the petrochemical industry. In particular, streams of ethylene or propylene may be used during the production of various polymers and chemicals. Such polymers and other chemicals include a wide range of plastics, consumer packaging materials, etc. Accordingly, there is a need for increased and economical production of ethylene and propylene.

SUMMARY

Described herein are methods for making ethylene and methods for making propylene from feedstocks that comprise butene. The methods utilize a butene-containing feed stream that, in some embodiments, may have a particular ratio of 1-butene to 2-butene depending on the desired product (i.e., ethylene or propylene). Generally, the butene-containing feed stream is metathesized, and then the metathesis products are separated into numerous streams. A C5+ olefin-containing stream is produced and passed to a cracking reactor. Additionally, other fractions from the separation are recycled in the process, as is described in detail herein. Such arrangements have been presently discovered to improve ethylene and/or propylene production efficiency and/or yields as compared to some other conventional methods that utilize a butene feedstock. Additionally, according to some embodiments, the same physical chemical conversion system may be utilized to selectively convert butene-containing feedstocks into ethylene or propylene utilizing the same or similar butene-containing feedstocks by controlling the ratio of 1-butene to 2-butene, as is described in detail herein. In such embodiments, an operator may select a target product based on relative value in the market.

According to one or more embodiments, butene may be converted to an ethylene-containing product by a process that may comprise passing a butene-containing feed stream to a metathesis reactor, wherein at least a portion of the butene-containing feed stream is metathesized in the metathesis reactor to form a metathesis effluent stream. The method may further comprise passing the metathesis effluent stream and a cracked effluent stream to a separation unit and forming a separated ethylene-containing stream, a separated propylene-containing stream, a separated butene-containing stream, and a separated C5+ olefin-containing stream. The separated ethylene-containing stream may exit the separation unit as the ethylene-containing product. The method may further comprise passing the separated C5+ olefin-containing stream to a cracking reactor, wherein at least a portion of the separated C5+ olefin-containing stream is cracked in the cracking reactor to form the cracked effluent stream. The method may further comprise recycling at least a portion of the separated propylene-containing stream and at least a portion of the separated butene-containing stream to the metathesis reactor.

According to one or more additional embodiments, butene may be converted to an propylene-containing product by a process that may comprise passing a butene-containing feed stream to a metathesis reactor, wherein at least a portion of the butene-containing feed stream is metathesized in the metathesis reactor to form a metathesis effluent stream. The method may further comprise passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated propylene-containing stream exits the separation unit as the propylene-containing product. The method may further comprise passing the separated C5+ olefin-containing stream to a cracking reactor, wherein at least a portion of the separated C5+ olefin-containing stream is cracked in the cracking reactor to form the cracked effluent stream. The method may further comprise recycling at least a portion of the separated ethylene-containing stream and at least a portion of the separated butene-containing stream to the metathesis reactor.

According to one or more yet additional embodiments, butene may be selectively converted to an ethylene-containing product and a propylene-containing product. The method may comprise operating a chemical conversion system to form the ethylene-containing product, stopping the operation of the chemical conversion system to form the ethylene-containing product, and operating the chemical conversion system to form the propylene-containing product. Operating a chemical conversion system to form the ethylene-containing product may be by a method comprising isomerizing the butene-containing feed stream to change the ratio of 1-butene to 2-butene in the butene-containing feed stream, passing a butene-containing feed stream to a metathesis reactor, wherein at least a portion of the butene-containing feed stream is metathesized in the metathesis reactor to form a metathesis effluent stream, passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated ethylene-containing stream exits the separation unit as the ethylene-containing product, passing the separated C5+ olefin-containing stream to a cracking reactor, wherein at least a portion of the separated C5+ olefin-containing stream is cracked in the cracking reactor to form the cracked effluent stream, and recycling at least a portion of the separated propylene-containing stream and at least a portion of the separated butene-containing stream to the metathesis reactor. Operating a chemical conversion system to form the propylene-containing product may be by a method comprising isomerizing the butene-containing feed stream to change the ratio of 1-butene to 2-butene in the butene-containing feed stream, passing a butene-containing feed stream to a metathesis reactor, wherein at least a portion of the butene-containing feed stream is metathesized in the metathesis reactor to form a metathesis effluent stream, passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated propylene-containing stream exits the separation unit as the propylene product, passing the separated C5+ olefin-containing stream to a cracking reactor, wherein at least a portion of the separated C5+ olefin-containing stream is cracked in the cracking reactor to form the cracked effluent stream, and recycling at least a portion of the separated ethylene-containing stream and at least a portion of the separated butene-containing stream to the metathesis reactor.

These and other embodiments are described in more detail in the Detailed Description. It is to be understood that both the foregoing general description and the following detailed description present embodiments of the subject technology, and are intended to provide an overview or framework for understanding the nature and character of the described technology as it is claimed. The accompanying drawings are included to provide a further understanding of the presently disclosed technology and are incorporated into and constitute a part of this specification. The drawings illustrate various embodiments and, together with the description, serve to explain the principles and operations of the presently described technology. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

Reference will now be made in greater detail to various embodiments, some embodiments of which are illustrated in the accompanying drawings. Whenever possible, the same reference numerals will be used throughout the drawings to refer to the same or similar parts.

Figure 1:
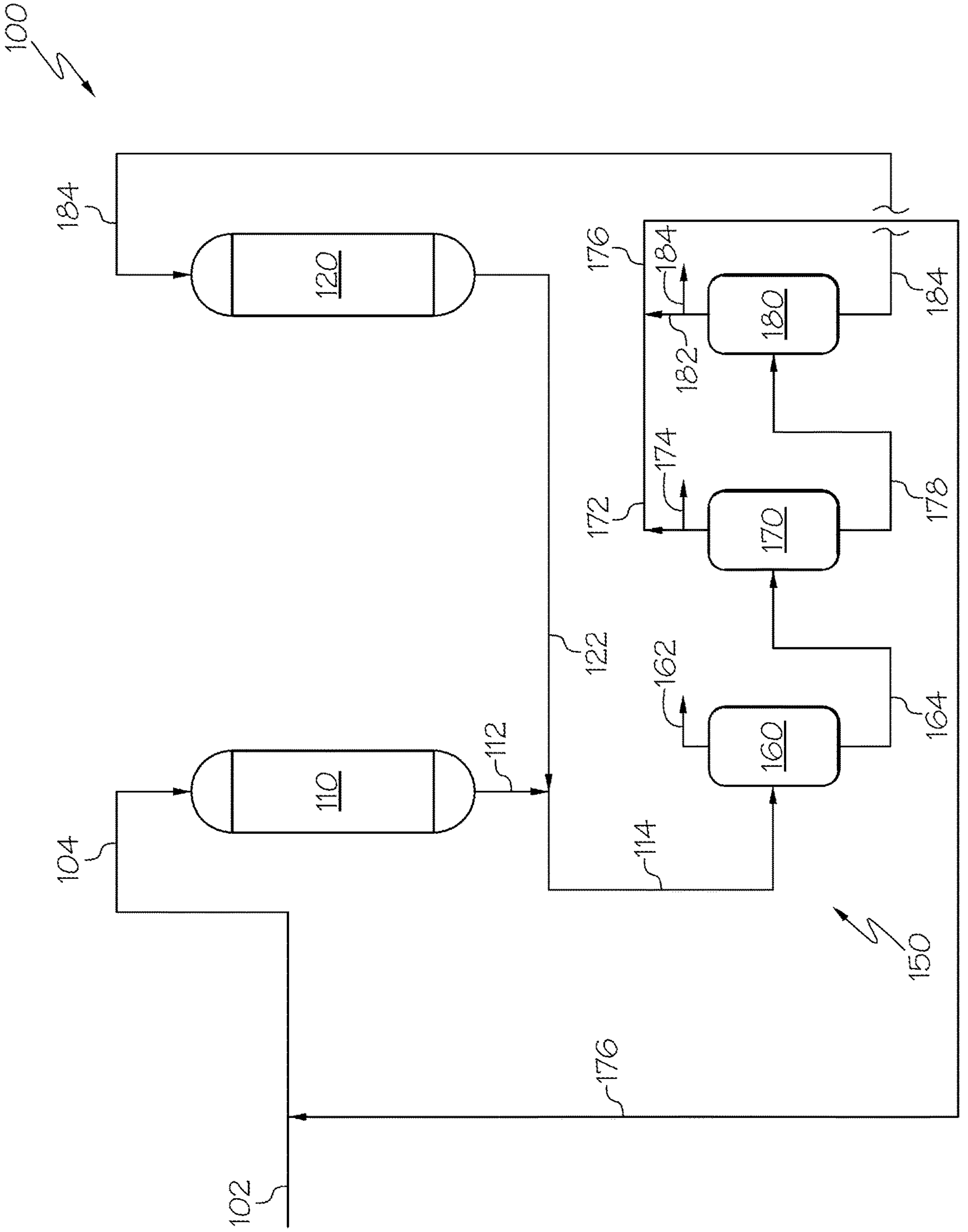
FIG. 1 schematically depicts a diagram of a butene conversion system for producing ethylene, according to one or more embodiments described in this disclosure.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydrocracking units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component. It should be understood that arrows in the relevant figures are not indicative of necessary or essential steps.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in one or more embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in some embodiments, less than all of the streams signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure relate to methods for making ethylene or propylene from butene feeds. In general, and as is discussed herein, the butene conversion system 100 of FIG. 1 receives butene and outputs ethylene as its major product, and the butene conversion system 192 of FIG. 3 receives butene and outputs propylene as its major product. The embodiments of FIGS. 2 and 4 are similar or identical to those of FIGS. 1 and 3, respectively, but additionally include an isomerization reactor that isomerizes at least a portion of the contents of the butene input stream to achieve a desired ratio of 1-butene to 2-butene. Description of the embodiments of FIGS. 1 and 2 may generally apply to the embodiments of FIGS. 3 and 4, as would be understood by those skilled in the art. For example, concepts disclosed herein applicable to FIG. 1 may be equally applicable to FIG. 3, and vice versa, even if not explicitly stated as such herein.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). For example, the "propylene-containing stream" includes propylene, and the "butene-containing stream" comprises butene. However, other chemicals may be present in such streams. For example, a "propylene-containing stream" may further include propane or other chemical species. It should also be understood that components of a stream are disclosed as passing from one system component to another system component (such as a separation unit or a reactor) when a stream comprising that component is disclosed as passing from that system component to another. For example, a disclosed "propylene-containing stream" passing from a first system component to a second system component should be understood to equivalently disclose "propylene" passing from a first system component to a second system component, and the like. Specific stream compositions, according to some embodiments, may be better understood in consideration with the Examples that follow.

As used in this disclosure, a "catalyst" refers to any substance which increases the rate of a specific chemical reaction. Catalysts described in this disclosure may be utilized to promote various reactions, such as, but not limited to, isomerization, metathesis, or cracking reactions, or combinations of these. As used in this disclosure, a "metathesis catalyst" increases the rate of a metathesis reaction, and a "cracking catalyst" increases the rate of a cracking reaction, and an "isomerization catalyst" increase of rate of isomerization. Such catalysts may have dual functionality in some embodiments. Examples of suitable catalysts can be found in, for example, U.S. Pat. No. 10,934,231, the disclosures of which are incorporated by reference herein. However, the methods described herein should not necessarily be limited by specific catalytic materials. As described herein, the catalysts, including those use for isomerization, metathesis, and cracking, may be fixed bed in configuration and utilize gaseous reactants. However, other configurations are contemplated.

As used in this disclosure, a "reactor," such as an isomerization reactor, a metathesis reactor, or a cracking reactor described herein, refers to a vessel in which one or more chemical reactions may occur between one or more reactants optionally in the presence of one or more catalysts. For example, a reactor may include a tank or tubular reactor configured to operate as a batch reactor, a gas phase reactor, a continuous stirred-tank reactor (CSTR), or a plug flow reactor. Example reactors include packed bed reactors such as fixed bed reactors, and fluidized bed reactors.

As used in this disclosure, a "separation unit" refers to any separation device or system of separation devices that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation.

Figure 2:
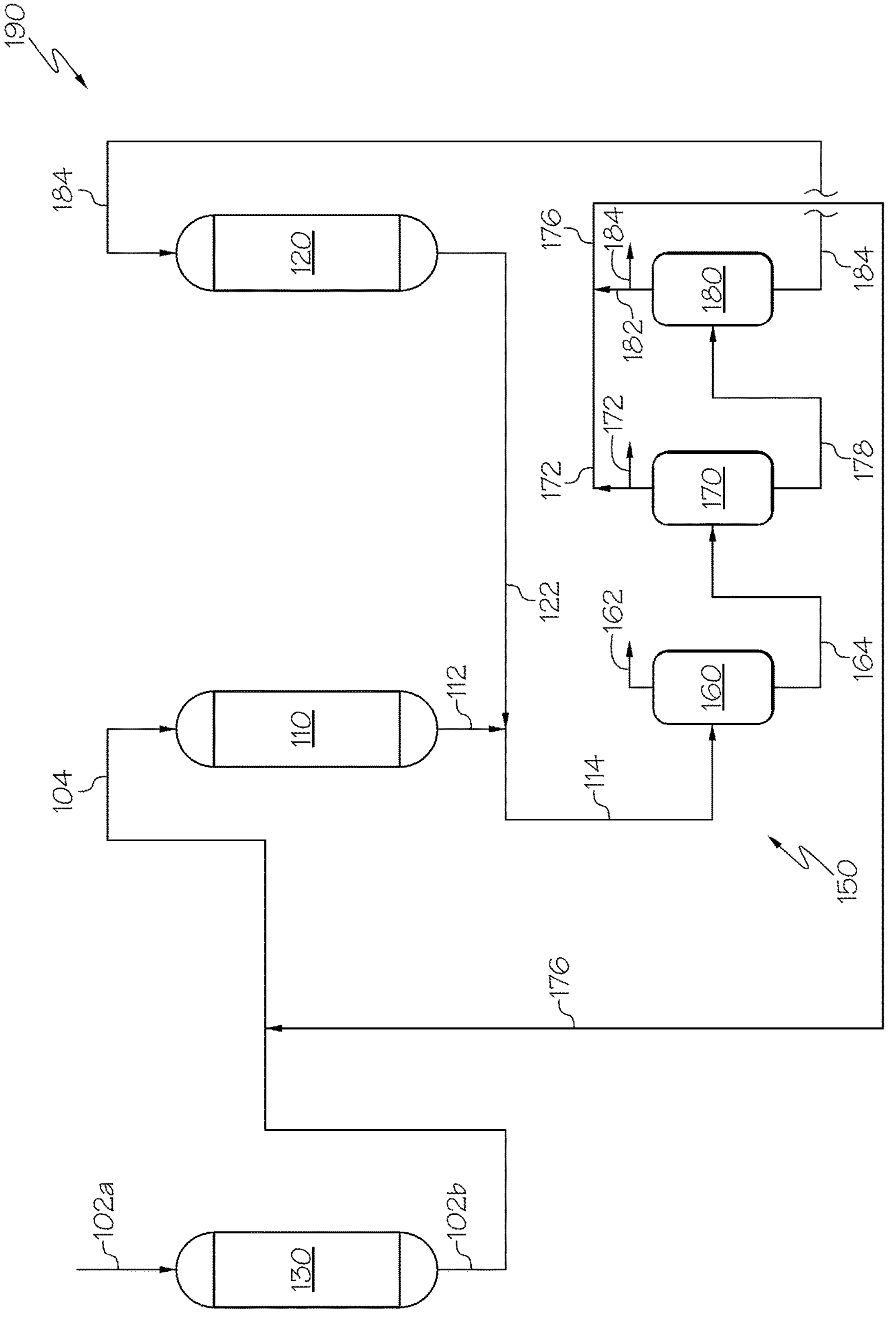
FIG. 2 schematically depicts a diagram of another butene conversion system for producing ethylene, according to one or more embodiments described in this disclosure.

Referring now to FIG. 1, the butene conversion system 100 for making ethylene may comprise a metathesis reactor 110, a cracking reactor 120, and a separation unit 150. As will be described herein, the separation unit 150 may include a de-ethyleneizer 160, a de-propyleneizer 170, and a debuteneizer 180. In general, the butene conversion system 100 is fed a butene-containing feed stream 102 and produces as a product stream a separated ethylene-containing stream 162. Such a product stream may be processed further downstream.

According to one or more embodiments, the butene-containing feed stream 102 may include one or more chemical species of butene (e.g., one or more isomers of butene). As described in this disclosure, "butene" may include at least 1-butene, isobutene, cis-2-butene, and trans-2-butene, and the terms "butene" and "butylene" may be used interchangeably in this disclosure. When "2-butene" is discussed herein, it may refer to trans-2-butene, cis-2-butene, or mixtures of each. In some embodiments, the butene-containing feed stream 102 includes only one isomer of butene, and in other embodiments the butene-containing feed stream 102 includes two or more of the isomers of butene. For example, the butene-containing feed stream 102 may comprise, consist essentially of, or consist of 1-butene, 2-butene (cis- and/or trans-2-butene), or a mixture of 1-butene and 2-butene. The butene-containing feed stream 102 may further comprise one or more butane species.

According to some embodiments, the butene-containing feed stream 102 may comprise a mixture of 1-butene and 2-butene. For example, the butene-containing feed stream 102 may comprise at least 50 wt. %, at least 75 wt. %, at least 90 wt. %, at least 95 wt. %, at least 99 wt. %, or even may consist of a mixture of 1-butene and 2-butene. It has been discovered that certain ratios of 1-butene to 2-butene in the butene-containing feed stream 102 may enhance, or even maximize, the ethylene-containing production yield of the butene conversion system 100. In particular, in some embodiments, the ratio of 1-butene to 2-butene in the butene-containing feed stream 102 may be from 0.5 to 1 to enhance ethylene-containing product production. For example, the ratio of 1-butene to 2-butene in the butene-containing feed stream 102 may be from 0.5 to 0.6, from 0.6 to 0.7, from 0.7 to 0.8, from 0.8 to 0.9, from 0.9 to 1.0, or any combination of these ranges.

Now referring to FIG. 2, an embodiment similar to the butene conversion system 100 of FIG. 1 is depicted. The butene conversion system 190 of FIG. 2 is generally identical to the butene conversion system 100 of FIG. 1, but additionally includes an isomerization reactor 130 that treats the input butene-containing feed stream 102*a* to form the isomerized butene-containing feed stream 102*b* that subsequently may be mixed with the recycle stream 176. The isomerization reactor 130 may isomerize some contents of the input butene-containing feed stream 102*a* such that the ratio of 1-butene to 2-butene in the isomerized butene-containing feed stream 102*b* can be manipulated and/or controlled. For example, in some embodiments, the input butene-containing feed stream 102*a* may comprise, consist essentially of, or consist of 1-butene, a portion of which may be converted to 2-butene. In other embodiments, input butene-containing feed stream 102*a* may comprise, consist essentially of, or consist of 2-butene, a portion of which may be converted to 1-butene. The isomerized butene-containing feed stream 102*b* may have a ratio of 1-butene to 2-butene from 0.5 to 1 to enhance ethylene product production, as described herein. Chemical Formula 1 depicts an example isomerization reaction in equilibrium between 1-butene and 2-butene.

Chemical Formula I

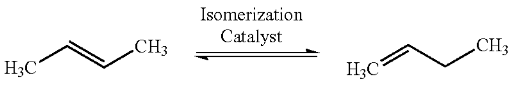

2-Butene 1-Butene

In one or more embodiments, the isomerization catalyst may be a metal oxide, such as MgO, CaO, other metal oxide or combinations of these. In one or more embodiments, the isomerization catalyst may be MgO. MgO is generally compatible with the mesoporous silica catalyst support impregnated with tungsten oxide, which is a metathesis catalyst that may be used in the metathesis reaction zone in embodiments. An increased isomerization of 2-butene to 1-butene by the MgO ensures sufficient availability of both 2-butene and 1-butene for the cross-metathesis reaction that takes place in the metathesis reaction zone, which may result in an ultimate increase in concentrations of propylene and C5+ olefins in the metathesis product stream. The C5+ olefins, such as pentene, are further catalytically cracked by the cracking catalyst in the cracking reaction zone to further increase the yield of propylene from the multiple-stage catalyst system 110. In one or more embodiments, CaO may be added as a co-catalyst to the MgO isomerization catalyst.

In some embodiments, the isomerization reactor 110 is a fixed bed reactor with full dedication to isomerization. Without being bound by theory, it is believed that such a dedicated isomerization reactor 110 may be beneficial as compared to some other, conventional isomerization techniques such as reactive distillation. As such, some embodiments described herein conduct isomerization without utilizing reactive distillation.

Referring now to FIGS. 1 and 2, the butene-containing feed stream 102 may be mixed with a recycle stream 176 to form a first mixed stream 104. The recycle stream 176 is described in detail hereinbelow, but generally the recycle stream 176 may comprise all or portions of the separated propylene-containing stream 172 and the separated butene-containing stream 182 exiting the separation unit 150. Accordingly, the first mixed stream 104 may comprise butenes and propylene. According to embodiments, the mass ratio of the butene-containing feed stream 102 and the recycle stream 176 in the first mixed stream 104 may vary. However, in some embodiments, the mass ratio of the butene-containing feed stream 102 and the recycle stream 176 in the first mixed stream 104 may be from 0.5 to 3, or from 0.6 to 2.

In embodiments, the first mixed stream 104 may be passed to the metathesis reactor 110, be processed in the metathesis reactor 110 by metathesis of the first mixed stream 104, such that at least a portion of the first mixed stream 104 is metathesized in the metathesis reactor 110 to form a metathesis effluent stream 112. The metatheses effluent stream 112 may exit the metathesis reactor 110. In some embodiments, the metathesis reactor 110 may utilize a catalyst to metathesize the first mixed stream 104. The metathesis reactor 110 may be a fixed bed reactor, but other reactor types are contemplated for use herein.

As used in this disclosure "metathesis" generally refers to a chemical reaction where fragments of alkenes (olefins) are redistributed by the scission and regeneration of alkene bonds, as is understood by those skilled in the art. Metathesis reactions may take place between the same isomers of butene, or between different isomers of butene. Moreover, metathesis may take place between butenes and propylene present in the first mixed stream 104. For example, cross-metathesis of 2-butene and 1-butene may be achieved as shown in Chemical Formula 2, for example, with the metathesis catalyst. As used in this disclosure, "cross-metathesis" refers to an organic reaction that involves the redistribution of fragments of alkenes by the scission and regeneration of carbon-carbon double bonds. In the case of 2-butenes and 1-butene, the redistribution of these carbon-carbon double bonds through metathesis may produce propylene and C5-C6 olefins (C5+ olefins). As described herein a "C #" where # is an integer, refers to a hydrocarbon with that integer number of carbon molecules, as would be understood by those skilled in the art. The metathesis catalyst may also isomerize 2-butenes to 1-butene through a "self-metathesis" reaction mechanism. Other metathesis reactions may also occur between butenes and propylene.

Chemical Formula 2

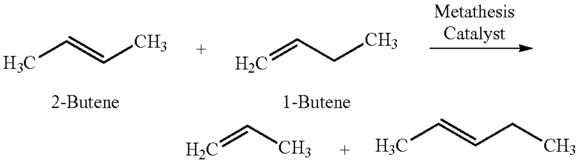

2-Butene 1-Butene

1-Propene 2-Pentene

According to embodiments, a relatively large portion of the butenes present in the first mixed stream 104 may be converted to other chemicals such as propylene and pentenes. For example, at least 10 wt. %, at least 20 wt. %, at least 30 wt. %, at least 40 wt. %, at least 50 wt. %, at least 60 wt. %, at least 70 wt. %, or even at least 80 wt. % of the butenes present in the first mixed stream 104 may be converted.

Non-limiting examples of metathesis catalysts and cracking catalysts, respectively, are disclosed in U.S. Pat. No. 10,532,347 entitled "Dual Catalyst System for Propylene Production," U.S. Pat. No. 10,005,703 entitled "Propylene Production Using a Mesoporous Silica Foam Metathesis Catalyst", and U.S. Pat. No. 10,934,231 entitled "Multiplestate catalyst systems and processes for propylene production," each of which are incorporated by reference in their entirety in this disclosure. As noted in those disclosures, suitable metathesis catalysts may include mesoporous silica catalysts impregnated with metal oxide. Suitable cracking catalysts may include mordenite framework inverted (MFI) structured silica catalysts. The mesoporous silica catalysts may include a pore size distribution of from about 2.5 nm to about 40 nm and a total pore volume of at least about 0.600 cm3/g (cubic centimeters per gram). However, it should be understood that the systems described in this disclosure may include any suitable metathesis catalysts and cracking catalysts, such as commercially available catalysts or catalysts which are the subject of future discovery.

According to one or more embodiments, the metathesis effluent stream 112, exiting the metathesis reactor 110, may comprise ethylene, propylene, 2-butenes, and/or pentenes. Additionally, the metathesis effluent stream 112 may comprise alkanes, such as those formed by the cracking reactor 120, discussed hereinbelow.

Still referring to FIG. 1, the metathesis effluent stream 112 may be passed from the metathesis reactor 110 and be combined with a cracked effluent stream 122 to form a second mixed stream 114. The cracked effluent stream 122 is described in detail hereinbelow, but generally the cracked effluent stream 122 comprises all or portions of the C5+ olefin stream 184 from the separation unit 150 after having been processed in the cracking reactor 120. The mass ratio of the metathesis effluent stream 112 and the cracked effluent stream 122 in the second mixed stream 114 may vary. However, in some embodiments, the mass ratio of the metathesis effluent stream 112 and the cracked effluent stream 122 in the second mixed stream 114 may be from 2.5 to 10, or from 3.3 to 5.

According to embodiments, the second mixed stream 114 may be passed to the separation unit 150. In some embodiments, such as that of FIGS. 1 and 2, the separation unit 150 includes three separators in series: the de-ethyleneizer 160, the de-propyleneizer 170, and the de-buteneizer 180. The de-ethyleneizer 160 may separate ethylene from heavier chemical species such as propylene, butene, and C5+ olefins. Ethylene is passed out of the de-ethyleneizer 160 via the separated ethylene-containing stream 162, which may be the primary product presently described process.

Still referring to FIG. 1, the de-ethyleneizer bottoms stream 164 may exit the de-ethyleneizer 160 and be passed to the de-propyleneizer 170. The de-propyleneizer 170 may separate propylene from heavier chemical species, such as butene and C5+ olefins. Propylene is passed out of the de-propyleneizer 170 as the separated propylene-containing stream 172. The de-propyleneizer bottoms stream 178 may exit the de-propyleneizer 170 and be passed to the de-buteneizer 180. The de-buteneizer 180 may separate butene from heavier chemical species, such as C5+ olefins. Butene is passed out of the de-buteneizer 180 as the separated butene-containing stream 182. The de-buteneizer bottoms stream 184 may exit the de-buteneizer 180 and comprise C5+ olefins. While the embodiment depicted in FIG. 1 is a suitable apparatus for separating the second mixed stream 114 into multiple components, it should be understood that other types of separation units may be suitable so long as they may separate the second mixed stream 114 into at least a separated ethylene-containing stream 162, a separated propylene-containing stream 172, a separated butene-containing stream 182, and a separated C5+ olefin-containing stream 184.

In one or more embodiments, and still referring to FIG. 1, the recycle stream 176, which is mixed with the butene-containing feed stream 102, may comprise at least a portion of the separated propylene-containing stream 172 and at least a portion of the separated butene-containing stream 182. Purge streams 174 and 184 may purge a limited amount of propylene and butene from the butene conversion system 100 to maintain system efficiency. The separated propylene-containing stream 172 and the separated butene-containing stream 182 may be mixed to from the recycle stream 176, and the recycle stream 176 is combined with the butene-containing feed stream 102. In other embodiments, the recycle stream 176 may be directly passed to the metathesis reactor. In other embodiments, the separated propylene-containing stream 172 and the separated butene-containing stream 182 may separately be combined with the butene-containing feed stream 102, or be passed directly to the metathesis reactor 110.

Additionally, referring now to FIG. 2, in embodiments where an isomerization reactor 130 is utilized, the recycle stream 176 is recycled back into the butene conversion system 100 downstream of the isomerization reactor 130.

Without being bound by theory, it is believed that the relatively light components of the second mixed stream 114 (i.e., butene and lighter) may be recycled without cracking. This avoids rather energy intensive cracking of relatively small molecules.

Referring again to FIG. 1, the C5+ olefin stream 184 may be passed from the de-buteneizer 180 to the cracking reactor 120. The C5+ olefin stream 184 may, in some embodiments, include 1-pentene and other C5+ olefins. In the cracking reactor 120, the C5+ olefin stream 184 may be cracked to form the cracked effluent stream 122, which exits the cracking reactor 120.

As used in this disclosure "cracking" generally refers to a chemical reaction where hydrocarbons molecules are decomposed into smaller hydrocarbons, such as by breaking of a single or double carbon-carbon bond. Cracking may also include the formation of alkanes from alkenes by the breaking of a double carbon-carbon bond to form a single carbon-carbon bond. Chemical Formula 3, below, depicts an example cracking reaction that may occur in the cracking reactor 120. Generally, the C5+ olefin stream 184 may include C5+ olefins, such as 2-pentene, which may be cracked into propylene, ethylene, butenes, and other alkanes, such as ethane, methane, propane, butane, etc.

Chemical Formula 3

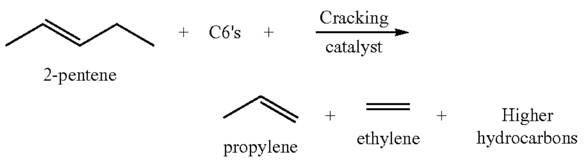

In one or more embodiments, the cracking catalyst may be a zeolite. In some embodiments, the cracking catalyst may be a structured zeolite, such as MFI or BEA structured zeolite, for example. In one or more embodiments, the cracking catalyst may be a MCM-41 catalyst or a SBA-15 catalyst. In one or more embodiments, the cracking catalyst may be an MFI structured silica catalyst. For example, the MFI structured silica-containing catalyst may include MFI structured aluminosilicate zeolite catalysts or MFI structured silica catalysts that do not contain alumina or are substantially free of alumina. In one or more embodiments, the MFI structured silica-containing catalyst includes alumina. In other embodiments, the MFI structured silica-containing catalyst is substantially free of alumina, having less than 1 wt. % alumina. In one or more embodiments, the MFI structured silica-containing catalysts may have less than 0.01 wt. % of alumina.

Moreover, it is contemplated that the MFI structured silica-containing catalyst may include other impregnated metal oxides in addition to or as an alternative to alumina. Like the mesoporous silica catalyst, the MFI structured silica-containing catalysts may have alumina, metal oxides, or both impregnated in the silica support. In addition to or as a substitute for alumina, it is contemplated that the MFI structured silica-containing catalyst includes one or more of the metal oxides previously listed in this disclosure, specifically, one or more oxides of a metal from Groups 6-10 of the IUPAC Periodic Table, more specifically, metal oxides of molybdenum, rhenium, tungsten, titanium, or combinations of these. It should be understood that the cracking catalyst may include a combination of multiple zeolites, such as zeolite particles which include multiple types of zeolites, or a mixture of zeolite particles where particles include different zeolites.

As depicted in FIG. 1, the cracked effluent stream 122 is combined with the metathesis effluent stream 112, from the metathesis reactor 110, to form the second mixed stream 114, which is then passed to the separation unit 150. According to embodiments, the entirety of the cracked effluent stream 122 (aside from the desired product such as ethylene) is recycled in the butene conversion system 100 via the recycle stream 176, meaning that the cracked effluent stream 122 includes all outputs of the cracking reactor 120, and all of this cracked effluent stream aside from system products are recycled.

Additionally, it is noted that the recycle stream 176 is recycled downstream of the isomerization reactor 130, in embodiments that utilized such, and upstream of the metathesis reactor 110. Such an arrangement may allow for cross metatheses reactions to form higher carbon olefins, which is much easier to be cracked into ethylene and propylene downstream. One function of the isomerization reactor 130 is to remove diene impurity in the feedstock. Since the recycled stream 176 do not have diene, there is no need to recycle to isomerization reactor 130 to dilute the effectiveness of the isomerization reactor.

Figure 3:
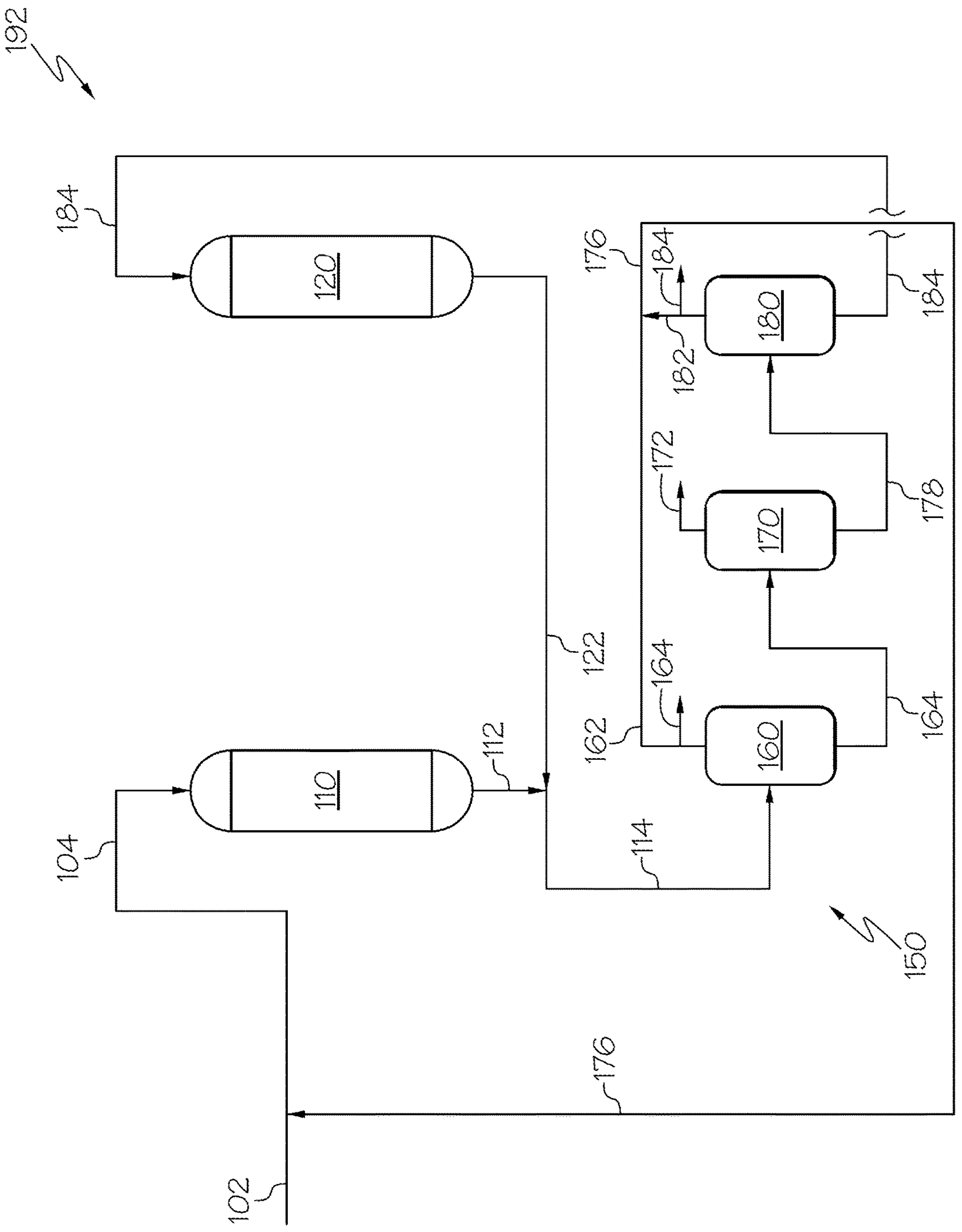
FIG. 3 schematically depicts a diagram of a butene conversion system for producing propylene, according to one or more embodiments described in this disclosure.
Figure 4:
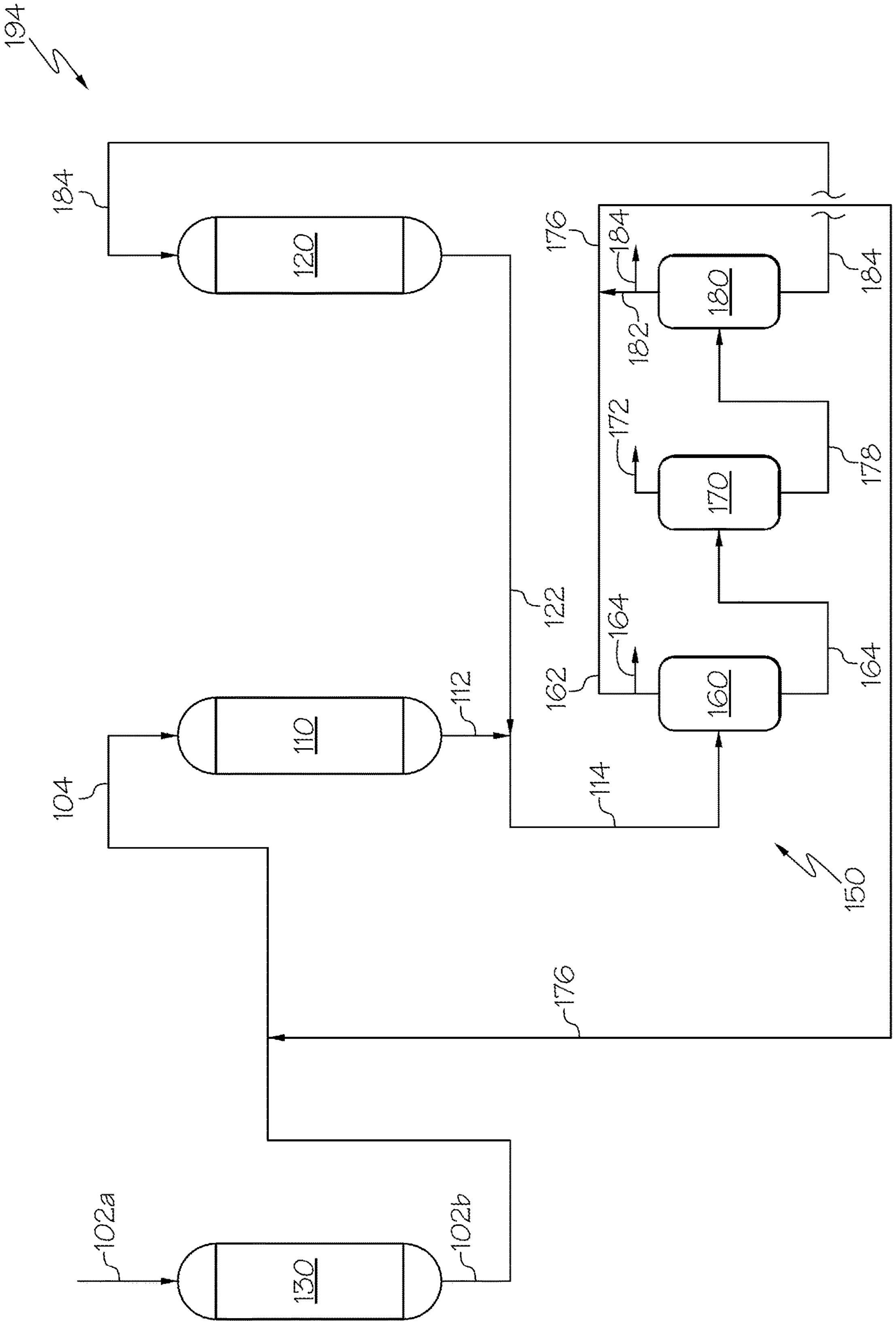
FIG. 4 schematically depicts a diagram of another butene conversion system for producing propylene, according to one or more embodiments described in this disclosure.

Now referring to FIG. 3, a butene conversion system 192 is depicted that is operable to make propylene as its primary product. The butene conversion system 192 of FIG. 3 and the butene conversion system 100 of FIG. 1 are similar in many respects, and like-numbered streams and system components are substantially identical in FIGS. 1 and 3. However, whereas in the butene conversion system 100 of FIG. 1 the separated ethylene-containing stream 162 is the major product stream, in the butene conversion system 192 of FIG. 3, the separated propylene-containing stream 172 is the major product stream. That is, in FIG. 3, the separated ethylene-containing stream 162 is combined with the separated butene-containing stream 182 to form the recycle stream 176, which is subsequently combined with the butene-containing feed stream 102, and purge stream 164 purges some limited amount of ethylene. However, operationally, the description of the butene conversion system 192 of FIG. 3 and the butene conversion system 100 of FIG. 1 are substitutable. For example, the metathesis reactor 110, cracking reactor 120, and separation unit 150 operate substantially identically the systems depicted by FIG. 1 and FIG. 3.

According to some embodiments, the butene-containing feed stream 102 of FIG. 3 may comprise a mixture of 1-butene and 2-butene. For example, the butene-containing feed stream 102 may comprise at least 50 wt. %, at least 75 wt. %, at least 90 wt. %, at least 95 wt. %, at least 99 wt. % of a mixture of 1-butene and 2-butenes, or even may consist of a mixture of 1-butene and 2-butene. It has been discovered that certain ratios of 1-butene to 2-butene in the butene-containing feed stream 102 may enhance, or even maximize, the propylene production yield of the butene conversion system 192. In particular, in some embodiments, the ratio of 1-butene to 2-butene in the butene-containing feed stream 102 may be from 0.2 to 0.5 to enhance propylene production. For example, the ratio of 1-butene to 2-butene in the butene-containing feed stream 102 may be from 0.2 to 0.3, from 0.3 to 0.4, from 0.4 to 0.5, or any combination of these ranges.

Now referring to FIG. 4, an embodiment similar to the butene conversion system 192 of FIG. 3 is depicted. The butene conversion system 194 of FIG. 4 is identical to the butene conversion system 192 of FIG. 3, but additionally includes an isomerization reactor 130 that treats the input butene-containing feed stream 102*a* to from the isomerized butene-containing feed stream 102*b* that subsequently is mixed with the recycle stream 176. The isomerization reactor 130 may isomerize some contents of the input butene-containing feed stream 102*a* such that the ratio of 1-butene to 2-butene in the isomerized butene-containing feed stream 102*b* can be manipulated, such that the ratio of 1-butene to 2-butene is from 0.2 to 0.5 to enhance propylene production as describe herein.

According to additional embodiments, the process described with respect to FIG. 2 and the process described with respect to FIG. 4 may be operated sequentially and alternated utilizing the same chemical conversion system in order to alter the product between ethylene and propylene. For example, if ethylene is a higher value chemical at a particular time, the scheme of FIG. 2 can be utilized and then switched to the scheme of FIG. 4 when propylene is a higher value chemical. The same or a substantially identical feedstock can be utilized to produce ethylene and propylene. However, as described herein, if ethylene is targeted as the primary product, then the ratio of 1-butene to 2-butene can be selectively altered by the isomerization reactor 130 as compared with of ratio of 1-butene to 2-butene when propylene is the targeted primary product. For example, when ethylene is the desired product, the chemical conversion system may operate as described with respect to FIG. 2 where the isomerized butene-containing feed stream 102*b* may have a ratio of 1-butene to 2-butene from 0.5 to 1 to enhance ethylene product production. On the other hand, when propylene is the desired product, the chemical conversion system may operate as described with respect to FIG. 4 where the isomerized butene-containing feed stream 102*b* may have a ratio of 1-butene to 2-butene from 0.2 to 0.5 to enhance propylene product production.

Several aspects are disclosed herein. A first aspect is a method for converting butene to an ethylene-containing product, the method comprising: passing a butene-containing feed stream to a metathesis reactor, wherein at least a portion of the butene-containing feed stream is metathesized in the metathesis reactor to form a metathesis effluent stream; passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated ethylene-containing stream exits the separation unit as the ethylene-containing product; passing the separated C5+ olefin-containing stream to a cracking reactor, wherein at least a portion of the separated C5+ olefin-containing stream is cracked in the cracking reactor to form the cracked effluent stream; and recycling at least a portion of the separated propylene-containing stream and at least a portion of the separated butene-containing stream to the metathesis reactor.

Another aspect includes any single or combination of above aspects, wherein the butene-containing feed stream comprises 1-butene and trans-2-butene.

Another aspect includes any single or combination of above aspects, wherein the weight ratio of 1-butene to 2-butene is from 0.5 to 1.

Another aspect includes any single or combination of above aspects, wherein the 2-butene is trans-2-butene.

Another aspect includes any single or combination of above aspects, further comprising isomerizing the butene-containing feed stream to change the ratio of 1-butene to 2-butene in the butene-containing feed stream.

Another aspect includes any single or combination of above aspects, wherein: at least a portion of the separated propylene-containing stream and at least a portion of the separated butene-containing stream are combined to form a recycle stream; and the butene-containing feed stream and the recycle stream are combined to form a first mixed stream, such that the butene-containing feed stream, at least a portion of the separated propylene-containing stream, and at least a portion of the separated butene-containing stream are passed to the metathesis reactor in the first mixed stream.

Another aspect includes any single or combination of above aspects, wherein the metathesis effluent stream and the cracked effluent stream are combined to form a second mixed stream, such that the metathesis effluent stream and the cracked effluent stream are passed to the separation unit in the second mixed stream.

Another aspect includes any single or combination of above aspects, wherein one or both of the metathesis reactor and the cracking reactor are fixed bed reactors.

Another aspect includes any single or combination of above aspects, wherein the separation unit comprises a de-ethyleneizer, a de-propyleneizer, and a de-buteneizer.

Another aspect is a method for converting butene to a propylene-containing product, the method comprising: passing a butene-containing feed stream to a metathesis reactor, wherein at least a portion of the butene-containing feed stream is metathesized in the metathesis reactor to form a metathesis effluent stream; passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated propylene-containing stream exits the separation unit as the propylene product; passing the separated C5+ olefin-containing stream to a cracking reactor, wherein at least a portion of the separated C5+ olefin-containing stream is cracked in the cracking reactor to form the cracked effluent stream; and recycling at least a portion of the separated ethylene-containing stream and at least a portion of the separated butene-containing stream to the metathesis reactor.

Another aspect includes any single or combination of above aspects, wherein the butene-containing feed stream comprises 1-butene and 2-butene.

Another aspect includes any single or combination of above aspects, wherein the weight ratio of 1-butene to 2 butene is from 0.2 to 0.5.

Another aspect includes any single or combination of above aspects, wherein the 2-butene is trans-2-butene.

Another aspect includes any single or combination of above aspects, further comprising isomerizing the butene-containing feed stream to change the ratio of 1-butene to 2-butene in the butene-containing feed stream.

Another aspect includes any single or combination of above aspects, wherein: at least a portion of the separated ethylene-containing stream and at least a portion of the separated butene-containing stream are combined to form a recycle stream; and the butene-containing feed stream and the recycle stream are combined to form a first mixed stream, such that the butene-containing feed stream, at least a portion of the separated ethylene-containing stream, and at least a portion of the separated butene-containing stream are passed to the metathesis reactor in the first mixed stream.

Another aspect includes any single or combination of above aspects, wherein the metathesis effluent stream and the cracked effluent stream are combined to form a second mixed stream, such that the metathesis effluent stream and the cracked effluent stream are passed to the separation unit in the second mixed stream.

Another aspect includes any single or combination of above aspects, wherein one or both of the metathesis reactor and the cracking reactor are fixed bed reactors.

Another aspect is a method for selectively converting butene to an ethylene-containing product and a propylene-containing product, the method comprising: operating a chemical conversion system to form the ethylene-containing product by a method comprising: isomerizing the butene-containing feed stream to change the ratio of 1-butene to 2-butene in the butene-containing feed stream; passing a butene-containing feed stream to a metathesis reactor, wherein at least a portion of the butene-containing feed stream is metathesized in the metathesis reactor to form a metathesis effluent stream; passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated ethylene-containing stream exits the separation unit as the ethylene-containing product; passing the separated C5+ olefin-containing stream to a cracking reactor, wherein at least a portion of the separated C5+ olefin-containing stream is cracked in the cracking reactor to form the cracked effluent stream; and recycling at least a portion of the separated propylene-containing stream and at least a portion of the separated butene-containing stream to the metathesis reactor; stopping the operation of the chemical conversion system to form the ethylene-containing product; operating the chemical conversion system to form the propylene-containing product by a method comprising: isomerizing the butene-containing feed stream to change the ratio of 1-butene to 2-butene in the butene-containing feed stream; passing a butene-containing feed stream to a metathesis reactor, wherein at least a portion of the butene-containing feed stream is metathesized in the metathesis reactor to form a metathesis effluent stream; passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated propylene-containing stream exits the separation unit as the propylene product; passing the separated C5+ olefin-containing stream to a cracking reactor, wherein at least a portion of the separated C5+ olefin-containing stream is cracked in the cracking reactor to form the cracked effluent stream; and recycling at least a portion of the separated ethylene-containing stream and at least a portion of the separated butene-containing stream to the metathesis reactor.

Another aspect includes any single or combination of above aspects, further comprising: stopping the operation of the chemical conversion system to form the propylene-containing product; and restarting the operation of the chemical conversion system to form the propylene-containing product.

Another aspect includes any single or combination of above aspects, wherein: the butene-containing feed stream passed to the metathesis reactor while operating the chemical conversion system to form the ethylene-containing product has a weight ratio of 1-butene to 2-butene of from 0.5 to 1; and the butene-containing feed stream passed to the metathesis reactor while operating the chemical conversion system to form the propylene-containing product has a weight ratio of 1-butene to 2-butene of from 0.2 to 0.5.

EXAMPLES

The various embodiments of methods and systems described herein will be further clarified by the following examples. The examples are illustrative in nature, and should not be understood to limit the subject matter of the present disclosure.

Example 1—Simulation of Embodiment of FIG. 4

Data from demonstration plant for metathesis reaction, data from literature from zeolite catalytic cracking and for isomerization were used to set up HYSYS process simulation model. One set of mass balance results for configuration of FIG. 4 is shown in Table 1. Table 2 shows the product yields of the same model.

TABLE 1

| | Stream Name | | | | | | | | | |
|---|---|---|---|---|---|---|---|---|---|---|
| | 102a | 102b | 112 | 122 | 184 | 182 | 162 | 172 | 184 | 164 |
| Mass Flow [kg/h] | 5610.8 | 5610.8 | 10970.5 | 11277.7 | 307.1 | 4573.9 | 785.9 | 4975.5 | 621.8 | 13.9 |
| Molecular Weight | 56.1 | 56.1 | 52.5 | 46.3 | 74 | 56.3 | 28.3 | 42 | 56.3 | 17.9 |
| Mass Density [kg/m3] | 1.9 | 1.8 | 1.1 | 0.8 | 636.1 | 626.3 | 528.7 | 608.8 | 626.3 | 1.6 |
| Components | | | | | | | | | | |
| Ethane [kg/h] | 0 | 0 | 96.88 | 115.55 | 0 | 0 | 96.88 | 18.6 | 0 | 0.01 |
| Methane [kg/h] | 0 | 0 | 0 | 10.46 | 0 | 0 | 0 | 0 | 0 | 10.46 |
| Propane [kg/h] | 0 | 0 | 1.01 | 28.72 | 0 | 1.01 | 0 | 27.24 | 0.14 | 0 |
| n-Butane [kg/h] | 0 | 0 | 267.4 | 304.57 | 0.11 | 267.4 | 0 | 0.05 | 36.53 | 0 |
| Ethylene [kg/h] | 0 | 0 | 230.84 | 697.92 | 0 | 0 | 688.05 | 3.01 | 0 | 3.41 |
| Propylene [kg/h] | 0 | 0 | 3491.24 | 4975.7 | 0 | 36.2 | 0.94 | 4925.57 | 4.94 | 0 |
| 1-Butene [kg/h] | 5610.77 | 4488.62 | 0 | 730.18 | 0.05 | 641.08 | 0 | 0.62 | 87.54 | 0 |
| i-Butene [kg/h] | 0 | 0 | 0 | 0 | 0 | 0 | 0 | 0 | 0 | 0 |
| Cis-2-Butene [kg/h] | 0 | 0 | 0 | 0 | 0 | 0 | 0 | 0 | 0 | 0 |
| Trans-2-Butene [kg/h] | 0 | 1122.15 | 3861.27 | 4006.03 | 2.15 | 3538.48 | 0 | 0.45 | 480.41 | 0 |
| 1-Pentene [kg/h] | 0 | 0 | 2213.95 | 306.96 | 203.96 | 89.71 | 0 | 0 | 12.26 | 0 |

TABLE 2

| Product distribution wt. % | | |
|---|---|---|
| Propylene (172) | Light purge (164) | C4 purge (184) |
| 88.67 | 0.25 | 11.08 |

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of." For example, the recitation of a composition "comprising" components A, B and C should be interpreted as also disclosing a composition "consisting of" components A, B, and C as well as a composition "consisting essentially of" components A, B, and C.

Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

It is also noted that recitations herein of "at least one" component, element, etc., should not be used to create an inference that the alternative use of the articles "a" or "an" should be limited to a single component, element, etc.

What is claimed is:

1. A method for converting butene to an ethylene-containing product, the method comprising:

passing a butene-containing feed stream to a metathesis reactor, wherein at least a portion of the butene-containing feed stream is metathesized in the metathesis reactor to form a metathesis effluent stream;

passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated ethylene-containing stream exits the separation unit as the ethylene-containing product;

passing the separated C5+ olefin-containing stream to a cracking reactor, wherein at least a portion of the separated C5+ olefin-containing stream is cracked in the cracking reactor to form the cracked effluent stream, wherein the C5+ olefin-containing stream consists of C5+ hydrocarbons, and the C5+ olefin-containing stream is the only stream passed to the cracking reactor; and recycling at least a portion of the separated propylene-containing stream and at least a portion of the separated butene-containing stream to the metathesis reactor.

2. The method of claim 1, wherein the butene-containing feed stream comprises 1-butene and 2-butene.

3. The method of claim 2, wherein the weight ratio of 1-butene to 2-butene is from 0.5 to 1.

4. The method of claim 2, wherein the 2-butene is trans-2-butene.

5. The method of claim 1, further comprising isomerizing the butene-containing feed stream to change the ratio of 1-butene to 2-butene in the butene-containing feed stream.

6. The method of claim 1, wherein:

at least a portion of the separated propylene-containing stream and at least a portion of the separated butene-containing stream are combined to form a recycle stream; and the butene-containing feed stream and the recycle stream are combined to form a first mixed stream, such that the butene-containing feed stream, at least a portion of the separated propylene-containing stream, and at least a portion of the separated butene-containing stream are passed to the metathesis reactor in the first mixed stream.

7. The method of claim 1, wherein the metathesis effluent stream and the cracked effluent stream are combined to form a second mixed stream, such that the metathesis effluent stream and the cracked effluent stream are passed to the separation unit in the second mixed stream.

8. The method of claim 1, wherein one or both of the metathesis reactor and the cracking reactor are fixed bed reactors.

9. The method of claim 1, wherein the separation unit comprises a de-ethyleneizer, a de-propyleneizer, and a de-buteneizer.

10. A method for converting butene to a propylene-containing product, the method comprising:

passing a butene-containing feed stream to a metathesis reactor, wherein at least a portion of the butene-containing feed stream is metathesized in the metathesis reactor to form a metathesis effluent stream;

passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated propylene-containing stream exits the separation unit as the propylene product;

passing the separated C5+ olefin-containing stream to a cracking reactor, wherein at least a portion of the separated C5+ olefin-containing stream is cracked in the cracking reactor to form the cracked effluent stream, wherein the C5+ olefin-containing stream consists of C5+ hydrocarbons, and the C5+ olefin-containing stream is the only stream passed to the cracking reactor; and recycling at least a portion of the separated ethylene-containing stream and at least a portion of the separated butene-containing stream to the metathesis reactor.

11. The method of claim 10, wherein the butene-containing feed stream comprises 1-butene and 2-butene.

12. The method of claim 11, wherein the weight ratio of 1-butene to 2 butene is from 0.2 to 0.5.

13. The method of claim 11, wherein the 2-butene is trans-2-butene.

14. The method of claim 10, further comprising isomerizing the butene-containing feed stream to change the ratio of 1-butene to 2-butene in the butene-containing feed stream.

15. The method of claim 10, wherein:

at least a portion of the separated ethylene-containing stream and at least a portion of the separated butene-containing stream are combined to form a recycle stream; and the butene-containing feed stream and the recycle stream are combined to form a first mixed stream, such that the butene-containing feed stream, at least a portion of the separated ethylene-containing stream, and at least a portion of the separated butene-containing stream are passed to the metathesis reactor in the first mixed stream.

16. The method of claim 10, wherein the metathesis effluent stream and the cracked effluent stream are combined to form a second mixed stream, such that the metathesis effluent stream and the cracked effluent stream are passed to the separation unit in the second mixed stream.

17. The method of claim 10, wherein one or both of the metathesis reactor and the cracking reactor are fixed bed reactors.

18. A method for selectively converting butene to an ethylene-containing product and a propylene-containing product, the method comprising:

operating a chemical conversion system to form the ethylene-containing product by a method comprising:

isomerizing the butene-containing feed stream to change the ratio of 1-butene to 2-butene in the butene-containing feed stream;

passing a butene-containing feed stream to a metathesis reactor, wherein at least a portion of the butene-containing feed stream is metathesized in the metathesis reactor to form a metathesis effluent stream;

passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated ethylene-containing stream exits the separation unit as the ethylene-containing product;

passing the separated C5+ olefin-containing stream to a cracking reactor, wherein at least a portion of the separated C5+ olefin-containing stream is cracked in the cracking reactor to form the cracked effluent stream; and recycling at least a portion of the separated propylene-containing stream and at least a portion of the separated butene-containing stream to the metathesis reactor;

stopping the operation of the chemical conversion system to form the ethylene-containing product;

operating the chemical conversion system to form the propylene-containing product by a method comprising:

isomerizing the butene-containing feed stream to change the ratio of 1-butene to 2-butene in the butene-containing feed stream;

passing a butene-containing feed stream to a metathesis reactor, wherein at least a portion of the butene-containing feed stream is metathesized in the metathesis reactor to form a metathesis effluent stream;

passing the metathesis effluent stream and a cracked effluent stream to a separation unit and forming a separated ethylene-containing stream, a separated propylene-containing stream, a separated butene-containing stream, and a separated C5+ olefin-containing stream, wherein the separated propylene-containing stream exits the separation unit as the propylene product;

passing the separated C5+ olefin-containing stream to a cracking reactor, wherein at least a portion of the separated C5+ olefin-containing stream is cracked in the cracking reactor to form the cracked effluent stream, wherein the C5+ olefin-containing stream consists of C5+ hydrocarbons, and the C5+ olefin-containing stream is the only stream passed to the cracking reactor; and recycling at least a portion of the separated ethylene-containing stream and at least a portion of the separated butene-containing stream to the metathesis reactor.

19. The method of claim 18, further comprising:

stopping the operation of the chemical conversion system to form the propylene-containing product; and restarting the operation of the chemical conversion system to form the propylene-containing product.

20. The method of claim 18, wherein:

the butene-containing feed stream passed to the metathesis reactor while operating the chemical conversion system to form the ethylene-containing product has a weight ratio of 1-butene to 2-butene of from 0.5 to 1; and the butene-containing feed stream passed to the metathesis reactor while operating the chemical conversion system to form the propylene-containing product has a weight ratio of 1-butene to 2-butene of from 0.2 to 0.5.

* * * * *